United States Patent [19]

Ragone

[11] Patent Number: 4,719,060
[45] Date of Patent: Jan. 12, 1988

[54] METHOD OF PREDICTING YARN PROPERTIES

[75] Inventor: Anthony S. Ragone, Seaford, Del.

[73] Assignee: E. I. Du Pont de Nemours and Company, Wilmington, Del.

[21] Appl. No.: 886,389

[22] Filed: Jul. 17, 1986

[51] Int. Cl.$^4$ .................. D01H 1/09; D01H 13/30
[52] U.S. Cl. ........................ 264/40.2; 8/400; 264/40.7; 264/78
[58] Field of Search ........... 73/160; 264/40.1, 40.2, 264/78; 356/28; 8/494; 364/151.2, 470, 473

[56] References Cited

U.S. PATENT DOCUMENTS

| | | | |
|---|---|---|---|
| 2,737,806 | 3/1956 | Dart et al. ............................ 73/160 |
| 2,939,201 | 6/1960 | Holland ....................... 264/177.13 X |
| 3,801,691 | 4/1974 | Brigmanis et al. ............. 264/177.13 |
| 3,929,013 | 12/1975 | Hendrix et al. ...................... 73/160 |
| 3,945,181 | 3/1976 | Yamazaki et al. .............. 73/160 X |
| 4,036,557 | 7/1977 | Christensen ......................... 356/28 |
| 4,101,612 | 7/1978 | Barker et al. ......................... 264/22 |
| 4,283,364 | 8/1981 | Capps et al. ..................... 264/176 F |
| 4,415,521 | 11/1983 | Mininni et al. ..................... 264/176 |
| 4,428,896 | 1/1984 | Stevenson ..................... 264/40.7 X |
| 4,586,934 | 5/1986 | Blalock et al. .................. 8/151.2 X |
| 4,632,548 | 12/1986 | Gunter, Jr. et al. ............. 356/28 X |

FOREIGN PATENT DOCUMENTS 2137191 12/1972 France .
2127544A 4/1984 United Kingdom .

*Primary Examiner*—Daniel M. Yasich

[57] ABSTRACT

A method for determining key yarn properties such as modification ratio and MBB dye uptake rate by measuring yarn bundle filament velocities near the spinneret as they are melt spun. The average filament velocities only are used to determine yarn properties from a calibration curve of yarn properties versus average filament velocity.

3 Claims, 6 Drawing Figures

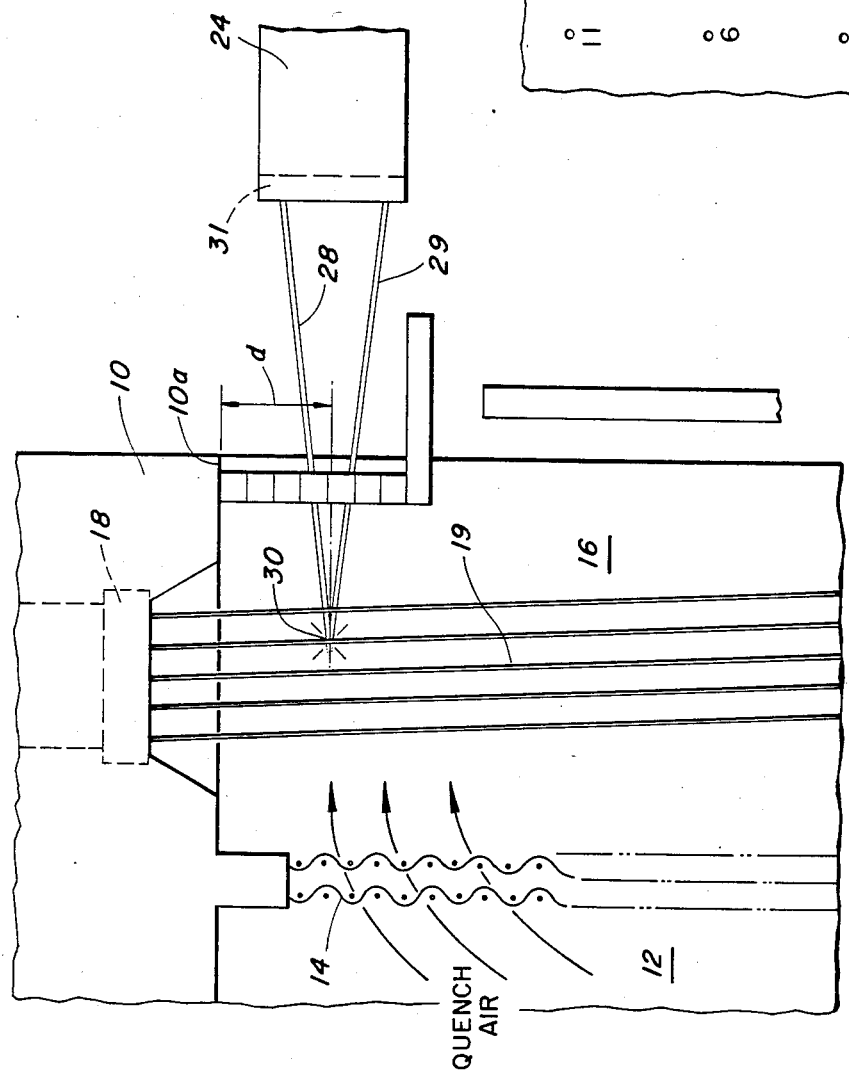

METHOD OF PREDICTING YARN PROPERTIES

BACKGROUND OF THE INVENTION

This invention relates generally to the production of filamentary structures and more particularly, it relates to a method for determining yarn property characteristics from velocity analysis of the yarn as it is spun.

Both yarn manufacturers and fabric producers are faced with the problem of variations in yarn properties (e.g., cross-section and dyeability) and the effect of these variations on fabrics. In the past, the effects of these variations in the actual fabric could only be determined by actually making test fabrics from the yarns which is expensive and time consuming. Now there are methods for simulating fabric appearance by just knowing the constituent yarn properties without having to make the actual fabric. However, measuring or determining yarn properties such as modification ratio and dyeability is also expensive and time consuming.

SUMMARY OF THE INVENTION

The present invention provides a method of determining yarn property characteristics such as modification ratio (MR) as disclosed in U.S. Pat. No. 2,939,201 col. 1 line 6 to col. 4 line 38 and Anthraquinone Milling Blue BL (MBB) dye uptake rate (MBB) by measuring filament velocities near the spinneret as the filaments are extruded into an air quenching zone below the spinneret. More particularly, the method involves measuring the velocity of some of the filaments extruded from the spinneret at a location where the filaments are partially quenched in the air quenching zone then averaging the velocities of the filaments measured and determining the MR or MBB dye uptake rate from a calibration curve based on the average filament velocity. Laser doppler velocimetry is used to provide a non-contact method for measuring the filament velocity.

The filaments of the bundle that are measured are important to the accuracy of the method. In the preferred embodiment the average positional property, such as MR or MBB is determined by averaging combinations of filament velocities. In a spinning machine wherein the quenching air flows from the back to the front of the spinneret in the quenching zone, the average filament velocities from the back and front rows of filaments provide excellent correlation with MR and MBB providing the same filaments are measured for each spinning position.

BRIEF DESCRIPTION OF THE DRAWINGS

FIG. 2 is an enlarged partial view of FIG. 1 showing the LDV aimed at a filament.

FIG. 2a is a plan view of the spinneret hole pattern of the spinneret of FIG. 2.

DETAILED DESCRIPTION OF THE ILLUSTRATED EMBODIMENT

Figure 1:
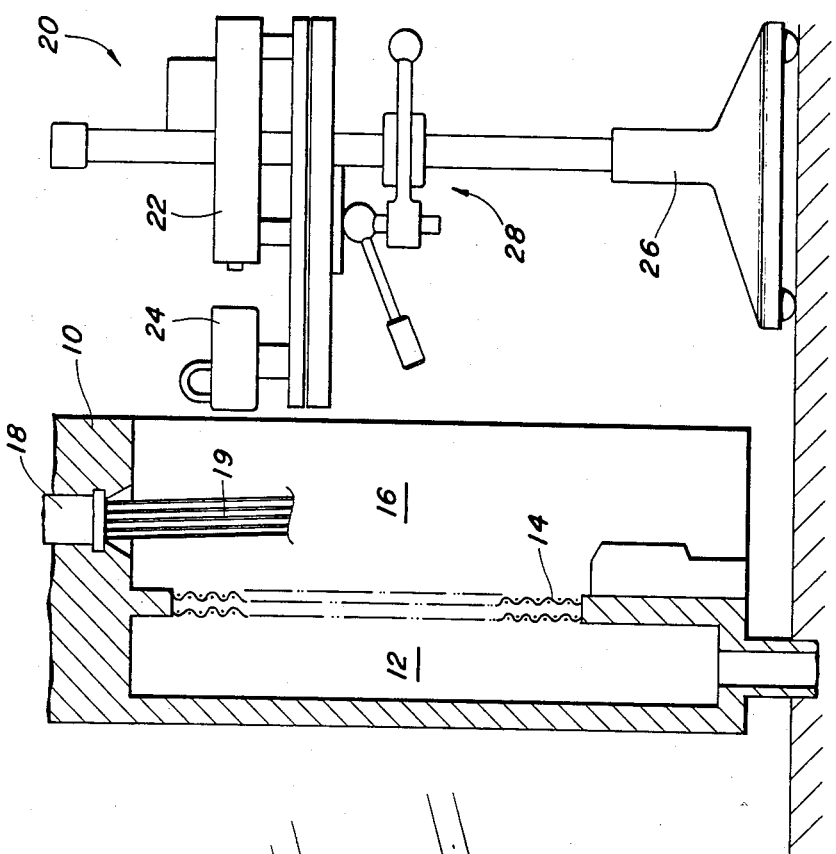
FIG. 1 is a schematic view of a laser doppler velocimeter (LDV) positioned adjacent a spinning machine quench zone for measuring filament velocity.

Referring to FIG. 1, the portion of a spinning machine chosen for purposes of illustration includes generally as components thereof, a support structure 10, a plenum chamber 12 located within the structure 10 and a foraminous member 14 separating the plenum chamber and a quenching zone 16. The numeral 18 designates a spinneret located at the top of quenching zone 16 through which molten polymer is extruded to form filaments 19. A portable laser doppler velocimeter (LDV), 9100 Series LDV by TSI of St. Paul, Minn., generally designated 20 is shown in front of the spinning position. The LDV 20 measures velocity by detecting the Doppler shift. The LDV includes a laser 22 (5 millewatt HeNe laser model No. 124B by Spectron Physics, Inc.) focused through an optic photomultiplier unit 24 all supported by a movable carriage 26 and its table 28 which has vertical as well as X-Y translation capability.

FIG. 2 shows the LDV in position in front of the spinning position and directed to a location at the upper portion of quenching zone 16. As can be seen a dual beam system (by TSI of St. Paul, Minn.) is used consisting of beams 28,29 intersecting at location 30. The location 30 is the focal point of lens 31 and consequently of laser light beams 28,29 (laser focus) and is adjusted to a distance d from the support surface 10a of from 1 to about 12 inches (2.54 to about 30.48 cm.).

Figure 3:
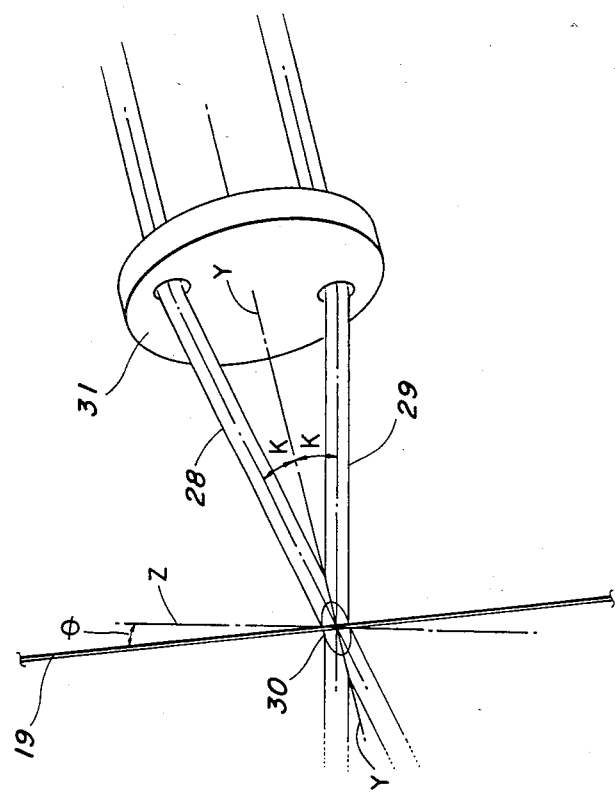
FIG. 3 shows the angular ($\theta$) relationship between a filament and the various axes associated with the laser beam.

Referring to FIG. 3, the angular relationship between a filament 19 and the axis associated with the laser beams 28,29 is shown. More particularly, K represents the angle between the optical axis Y of the lens 31 and each of the laser light beams 28,29. The axis designated Z is perpendicular to the Y axis and in the plane of the laser beams 28,29 and the angle $\theta$ is the angle from filament 19 to the Z axis.

For the illustrated embodiment a 13 filament threadline is illustrated and the filaments are designated 1 through 13 as shown in FIG. 2a.

In operation, when measuring filament speeds, certain filaments of the threadline are chosen: two front (e.g., filament Nos. 1 and 3) and two rear (e.g., filament Nos. 11 and 13). Each of the four filaments is illuminated with the laser focus then the scattered laser light is converted to an analog signal representative of the doppler frequency ($F_d$) which in turn represents the yarn speed as a function of the particular lens used.

The yarn velocity is calculated from the doppler frequencies via the equation below.

$$V = F_d * wl / (\text{SIN}(K) * \text{COS}(\theta)) \qquad (1)$$

V is the yarn velocity, yards per minute; (YPM),
wl is the HeNe laser wavelength, 6328 angstroms or 6.328×10$^{-5}$ cm
$F_d$ is the measured doppler frequency, in MHz
K is the laser-to-lens axis angle (FIG. 3)
$\theta$ is the filament to Z-axis angle (FIG. 3).

TEST METHODS

MBB dye uptake

For MBB dye uptake rate testing in the following example yarn samples are prepared by loosely winding 3.00 gram skeins. Thirty-six of these skeins, consisting of 6 control samples and 30 test samples, are scoured by immersing them in a vessel containing 21 liters of room temperature scouring solution comprised of 160 ml ammonium hydroxide, 100 ml 10% Merpol HCS, (a liquid, nonionic detergent from E. I. du Pont de Nemours and Co.), with the remainder of the solution being demineralized water. This bath has a pH of 10.4. The bath containing the yarn samples is heated to 95° C. at the rate of 3° per minute. The samples are removed and the bath discarded when the temperature reaches 95° C.

The yarns are then dyed by placing the 36 samples in 21 liters of an aqueous dye solution comprised of 200 ml of a standard buffer solution at 3.8 pH, 100 ml of 10% Merpol HCS (a liquid, nonionic detergent from E. I. du Pont de Nemours and Co.,), 5 ml Depuma (a silicone defoaming agent), and 500 ml of 0.18% Anthraquinone Milling Blue BL (abbreviated MBB) (C.I. Acid Blue 122). The final bath pH is 4.4. The solution temperature is increased at 3°/min from room temperature to 75° C., and held at that temperature for 30 minutes. The dyed samples are rinsed, dried, and measured for dye depth by reflecting colorimeter.

The dye values are determined by computing K/S values from reflectance readings. The equations are:

$$MBB \text{ dyeability} = \frac{K/S \text{ sample}}{K/S \text{ control}} \times 180 \text{ and } K/S = \frac{(1-R)^2}{2R}$$

when R = the reflectance value. The 180 value is used to adjust and normalize the control sample dyeability to a known base.

Modification Ratio

To determine modification ratio (MR) a thin slice of each yarn was cut perpendicular to its longitudinal axis with a microtome and mounted on a microscope slide by techniques well known in the art. Two photomicrographs of each yarn cross-section were made at a magnification such that together the two photomicrographs clearly showed each of the 13 filaments making up the yarn bundle. The perimeter of the image of the individual filaments on the photomicrographs was traced using a commercial digitizer (such a Numonics Model 224). The digitizer translates the perimeter tracing into x-y data pairs from which MR is calculated using a small computer.

EXAMPLE

Four 40-13 T-865 semi-dull trilobal nylon filament yarns were prepared. The filament MBB dye rate and MR of these yarns was determined by the above-known methods and by the present invention.

Accordingly, for the four yarns the filament Nos. 1, 3, 11 and 13 (FIG. 2a) are measured with the laser velocimeter described herein. The average velocity per yarn line is recorded in Table I for each yarn.

TABLE I

| Yarn Line | Filament No. | Signal Frequency MHz | Average Velocity/yarn line YPM |
|---|---|---|---|
| 1 | 1 | .191 | 120.8 |
|   | 3 | .204 |   |
|   | 11 | .256 |   |
|   | 13 | .258 |   |
| 2 | 1 | .190 | 121.2 |
|   | 3 | .202 |   |
|   | 11 | .260 |   |
|   | 13 | .270 |   |
| 3 | 1 | .188 | 118.8 |

TABLE I-continued

| Yarn Line | Filament No. | Signal Frequency MHz | Average Velocity/yarn line YPM |
|---|---|---|---|
|   | 3 | .198 |   |
|   | 11 | .249 |   |
|   | 13 | .269 |   |
| 4 | 1 | .182 | 109.9 |
|   | 3 | .188 |   |
|   | 11 | .232 |   |
|   | 13 | .225 |   |

Figure 4:
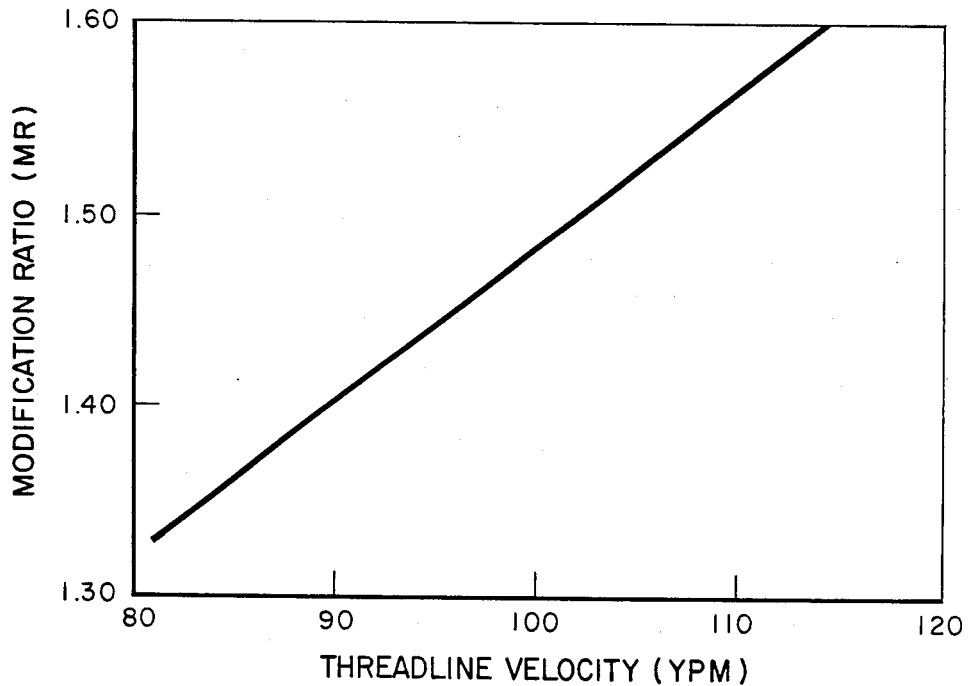
FIG. 4 is a graph showing correlation between MR and yarn velocity as per the example.

In FIG. 4 is plotted yarn line velocity versus MR values determined by the digitizer. A straight line of the form $\overline{V} = aMR + b$ with a high correlation coefficient is obtained over a range of MR values.

Figure 5:
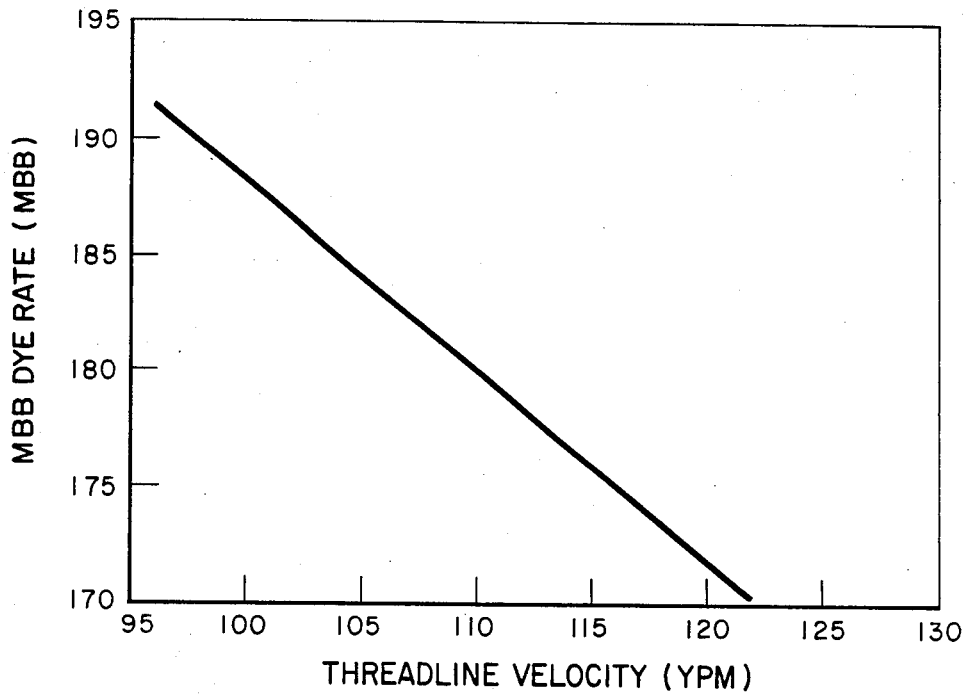
FIG. 5 is a graph showing correlation between MBB and yarn velocity as per the example.

In FIG. 5 is plotted yarn line velocity values versus MBB values determined by the test method defined herein. Again, a straight line with a high correlation coefficient is obtained.

MR values and MBB dye uptake rate values are then determined by measuring $\overline{V}$ as just described and using the calibration graphs (FIGS. 4 and 5).

While the invention has been disclosed with velocity measurements of two filaments in the back row and two filaments in the front row, other combinations of filament velocities provide very good correlation with MBB dye uptake rate and MR.

I claim:

1. A method of predicting the modification ratio of trilobal filaments being extruded in a path into an air quenching zone below the spinneret, said method comprising the steps of:
   (a) measuring the velocity of a portion of said filaments extruded from said spinneret at a location where said filaments are partially quenched;
   (b) averaging the velocities of said filaments measured;
   (c) determining the modification ratio of said filaments using the perimeter of the image of each filament from which modification ratio is calculated in a known manner;
   (d) plotting average filament velocity versus modification ratio values determined according to step (c) for a range of velocities to establish a calibration curve, said curve being a straight line function with a high correlation coefficient, and
   (e) determining the modification ratio of said filaments from velocity measurements only as specified in steps (a) and (b) from said calibration curve.

2. A method of determining MBB dye rate of filaments being extruded into an air quenching zone below the spinneret, said method comprising the steps of:
   (a) measuring the velocity of a portion of said filaments extruded from said spinneret at a location where said filaments are partially quenched;
   (b) averaging the velocities of said filaments measured; and
   (c) determining MBB dye rate of said filaments by dyeing the filaments and measuring them for dye depth using a colorimeter in a known manner;
   (d) plotting average filament velocity versus MBB dye rate values determined according to step (c) for a range of velocities of said filaments to establish a calibration curve, said curve being a straight line function with a high correlation coefficient; and
   (e) determining the MBB dye rate of the filaments from velocity measurements only as specified in steps (a) and (b) from said calibration curve.

3. The method as defined in claim 1 or 2, said location being from about 1 to about 12 inches below said spinneret.

* * * * *